US009066915B2

(12) United States Patent
Myers et al.

(10) Patent No.: US 9,066,915 B2
(45) Date of Patent: Jun. 30, 2015

(54) MEAL REPLACEMENT COMPOSITIONS AND WEIGHT CONTROL METHOD

(76) Inventors: Michael D. Myers, Huntington Beach, CA (US); David Sack, Huntington Beach, CA (US)

( * ) Notice: Subject to any disclaimer, the term of this patent is extended or adjusted under 35 U.S.C. 154(b) by 1579 days.

(21) Appl. No.: 11/866,610

(22) Filed: Oct. 3, 2007

(65) Prior Publication Data

US 2008/0081840 A1 Apr. 3, 2008

Related U.S. Application Data

(60) Provisional application No. 60/886,901, filed on Jan. 26, 2007, provisional application No. 60/827,979, filed on Oct. 3, 2006.

(51) Int. Cl.
*A61K 31/20* (2006.01)
*A61K 31/202* (2006.01)
*A23D 9/00* (2006.01)
*A23L 1/29* (2006.01)

(52) U.S. Cl.
CPC .............. *A61K 31/20* (2013.01); *A61K 31/202* (2013.01); *A23D 9/00* (2013.01); *A23L 1/296* (2013.01); *A23V 2002/00* (2013.01)

(58) Field of Classification Search
CPC .................................................. A61K 31/202
USPC ................................................ 514/183, 549
See application file for complete search history.

(56) References Cited

U.S. PATENT DOCUMENTS

| 5,360,618 | A | * | 11/1994 | Walker ............................ 426/72 |
| 6,140,304 | A | | 10/2000 | Sears |
| 7,025,984 | B1 | | 4/2006 | Jandacek et al. |
| 2004/0092590 | A1 | * | 5/2004 | Arterburn et al. ............. 514/560 |
| 2004/0214772 | A1 | * | 10/2004 | Quay et al. ...................... 514/12 |

FOREIGN PATENT DOCUMENTS

| KR | 1020040063616 | | 7/2004 |
| WO | WO2004012727 | A1 | 2/2004 |
| WO | WO2006017627 | A3 | 2/2006 |
| WO | WO2007008384 | A2 | 1/2007 |
| WO | WO2007070611 | A2 | 6/2007 |
| WO | WO2007100561 | A2 | 9/2007 |
| WO | WO2007135141 | A1 | 11/2007 |

OTHER PUBLICATIONS

Kunesova et al., The influence of n-3 Polyunsaturated Fatty Acids and Very Low Calorie Diet during a Short-term Weight Reducing Regimen on Weight Loss and Serum Fatty Acid Composition in Severely Obese Women, 2006, Physiol. Res., vol. 55, pp. 63-72.*
Uenishi et al., Anti-obesity effect of soy milk containing decosahexaenoic acid in young Japanese adult women, 2002, Nippon Eiyo, Shokuryo Gakkai, vol. 55, No. 6, pp. 339-345. Abstract Only Provided.*
Marian Burros, Diet Formulas: Losing the Weight Is the Easy Part, 1988, The New York Times, pp. 1-3. Accessed on Oct. 29, 2010 on http://www.nytimes.com/1988/07/06/garden/diet-formulas-losing-the-weight-is-the-easy-part.html.*
McVeigh et al., Endothelial-dependent vasodilation in chronic heart failure is improved by dietary fish oil supplementation, 2003, FASEB Journal, vol. 17, No. 4-5, pp. Absract No. 769.3. Abstract Only.*
Ruzickova et al., Omega-3 PUFA of Marine Origin Limit Diet Induced Obesity in Mice by Reducing Cellularity of Adipose Tissue, 2004, Lipids, vol. 39, pp. 1177-1185.*
Chan et al., Randomized controlled trial of the effect of n-3 fatty acid supplementation on the metabolism of apolipoprotein B100 and chylomicron remnants in men with visceral obesity, 2003, Am J Clin Nutr, vol. 77, pp. 300-307.*
English Translation of Uenishi et al. "Anti-obesity effect of Soy Milk containing Docosahexaenoic acid in Young Japanese Adult Women". pp. 1-16.*
Kunesova, M. et al., "The Influence of n-3 Polyunsaturated Fatty Acids and Very Low Calorie Diet during a Short-term Weight Reducing Regimen on Weight Loss and Serum Fatty Acid Composition in Severely Obese Women," Physiol. Res. 55: 63-72 (2006).
Hulbert, A.J., et al., "Dietary Fats and Membrane Function: Implications for Metabolism and Disease," Biol. Rev. 80:155-169 (2005).
Apolzan, John W., et al., "Inadequate Dietary Protein Increases Hunger and Desire to Eat in Younger and Older Men," The Journal of Nutrition 137:1478-1482 (2007).
Clifton, Peter M., "Very Low-Fat (12%) and High Monounsaturated Fat (35%) Diets Do Not Differentially Affect Abdominal Fat Loss in Overweight, Nondiabetic Women," American Society for Nutritional Sciences 2004, pp. 1741-1745.
Supplementary European Search Report issued in European Patent Application No. 07 85 3753 dated Jan. 4, 2010.
Nelson, Gary, J., Nutrition REseasrch, vol. 9, p. 531-544, 1989.
Du, Chunyan, et al., Journal of Nutritional Biochemistry 15 (2004) 273-280.
PCT/US2007/080326, Written Opinion, dated Mar. 20, 2008.
PCT/US2007/080326, International Search Report, dated Mar. 20, 2008.
PCT/US2007/080326, International Preliminary Report on Patentability, dated Apr. 7, 2009.
Burns, Rebecca and Moniri, Nader, "Agonism with the omega-3 fatty acids a-linolenic acid and docosahexaenoic acid mediates phosphorylation of both the short and long isoforms of the human GPR120 receptor," Biochemical and Biophysical Research Communications, 396 (2010) 1030-1035.
Parra, D. et al. "A diet rich in long chain omega-3 fatty acids modulates satiety in overweight and obese volunteers during weight loss," Appetite 51 (2008) 676-680.

* cited by examiner

*Primary Examiner* — James D Anderson
*Assistant Examiner* — Meghan Finn
(74) *Attorney, Agent, or Firm* — Michael Fedrick; Loza & Loza, LLP

(57) ABSTRACT

A food composition having a high protein level and comprising DHA, preferably for use as a meal replacement, is administered to subjects in order to control their weight.

12 Claims, 4 Drawing Sheets

MEAL REPLACEMENT COMPOSITIONS AND WEIGHT CONTROL METHOD

CROSS-REFERENCE TO RELATED APPLICATIONS

The present application claims the benefit of priority from U.S. Provisional Patent Application No. 60/886,901, titled "MEAL REPLACEMENT COMPOSITIONS AND WEIGHT CONTROL METHOD" and filed Jan. 26, 2007, and from U.S. Provisional Patent Application No. 60/827,979, titled "MEAL REPLACEMENT COMPOSITIONS AND WEIGHT CONTROL METHOD" and filed Oct. 3, 2006. The entire disclosure of each of the foregoing applications is hereby incorporated into this application by reference in its entirety.

BACKGROUND

Health experts recognize that excess body weight, particularly if acquired early in life, can be a major health hazard. Excess weight is a risk factor for heart disease, some cancers, hypertension, hyperlipidemia, type 2 diabetes, and other serious metabolic disorders. It also causes additional strain on weight-bearing joints such as the knees and spine, and in many other ways can impair one's health. The effective treatment of obesity, however, remains a largely unachieved goal.

Currently, many medical and non-medical weight reduction programs utilize portion-controlled meal replacement products that are relatively low in calories. Examples of such products are the OPTIFAST, MEDIFAST, HMR, HEALTHWISE, PROCAL, and SLIMFAST food products. These portion-controlled products accomplish weight loss by limiting the caloric intake of an individual when used as instructed.

Some attempts have been made to increase fat utilization by adding monounsaturated fats to foods, but these attempts have been unsuccessful [see, e.g., Clifton P M, Noakes M, Keogh J B, "Very low-fat (12%) and high monounsaturated fat (35%) diets do not differentially affect abdominal fat loss in overweight, nondiabetic women," J. Nutr., 134:1741-5 (2004)]. The use of n-3 highly unsaturated fatty acids in a weight-loss program has also been reported [Kunesova M, et al., "The Influence of n-3 Polyunsaturated Fatty Acids and Very Low Calorie Diet during a Short-term Weight Reducing Regimen on Weight Loss and Serum Fatty Acid Composition in Severely Obese Women," Physiol. Res. 55: 63-72 (2006)].

SUMMARY

While calorie reduction leads to preferential loss of body fat when adequate protein and other nutrients are present in an individual's diet, compensatory homeostatic mechanisms appear to lower resting metabolic rates in individuals undergoing energy-restricted diets, thereby slowing the rate of further weight loss. An additional problem is that subjects undergoing meal replacement diets report that they fail to adhere to such regimens over time due to feelings of hunger. Thus, there remains a need for improved meal replacement compositions and weight control methods to facilitate weight control in individuals in need of weight control.

The present method of managing the body weight of a subject and achieving weight control involves increasing the satiety of the subject by orally administering DHA to the subject in an amount of at least about 1100 milligrams per day in a diet comprising up to about 1200 calories. The diet can be a low calorie diet comprising between about 800 and about 1200 calories, but can also be a very low calorie diet comprising fewer than 800 calories. The subject's protein, carbohydrate, and fat calories should be in a ratio such that the number of calories provided by protein in the diet compared to the number of calories provided by carbohydrate and fat produces a ratio of at least 0.5:1, and preferably between about 0.7:1 and about 1.6:1. The DHA is preferably administered to the subject according to this method for at least 2 weeks, and more preferably for at least 4 weeks.

The amount of DHA consumed daily by a subject in the present methods can be 1800 milligrams, 2500 milligrams, or more. Preferably, the DHA is consumed at each serving in an amount of at least about 230 milligrams, and more preferably in an amount of at least about 400 milligrams of DHA. In one particular embodiment, the DHA is consumed five times per day in a food composition comprising about 100 calories and about 230 milligrams of DHA. A nutritional composition comprising DHA can be in the form of a powder which is reconstitutable in water, or alternatively can be a liquid solution or a suspension.

DHA for use in the present methods can be present, for example, in a processed food composition, comprising between about 60 and 300 calories, between about 6 and 35 grams of protein, between about 1 and 30 grams of carbohydrate, and between about 1 and 6 grams of fat. The fat component comprises between about 100 and about 1000 milligrams DHA, and the number of calories provided by protein in the composition compared to the number of calories provided by carbohydrate and fat produces a ratio of at least 0.5:1, and more preferably produces a ratio of between about 0.7:1 and about 1.6:1. The composition can comprise about 230 milligrams of DHA in a serving, and more preferably about 400 milligrams of DHA. The composition can also be in powder form, the powder being reconstitutable in water, or can be a liquid solution or suspension. In one particular embodiment, the composition comprises about 15 grams of protein, about 7 grams of carbohydrate, and about 1 gram of fat, including about 230 milligrams DHA.

DRAWINGS

These and other features, aspects and advantages of the present invention will become better understood with regard to the following description, appended claims, and accompanying figures.

Figure 1:
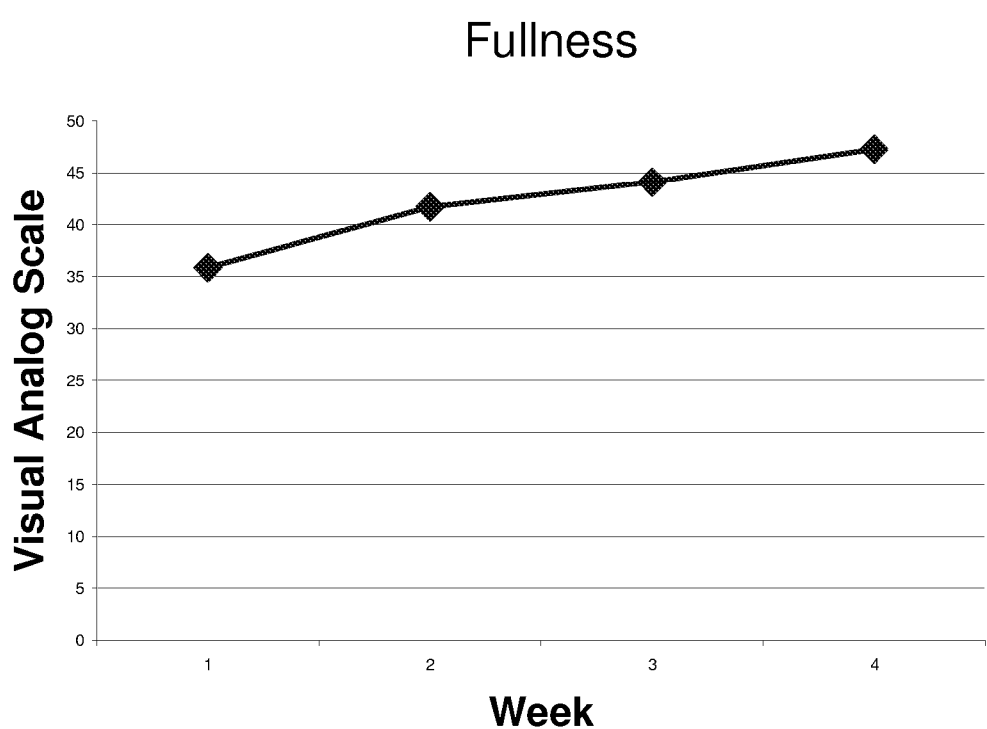
FIG. 1 is a chart showing changes in subjects' experience of satiety during a study described in Example 1 below in which the subjects consumed the present food composition.
Figure 2:
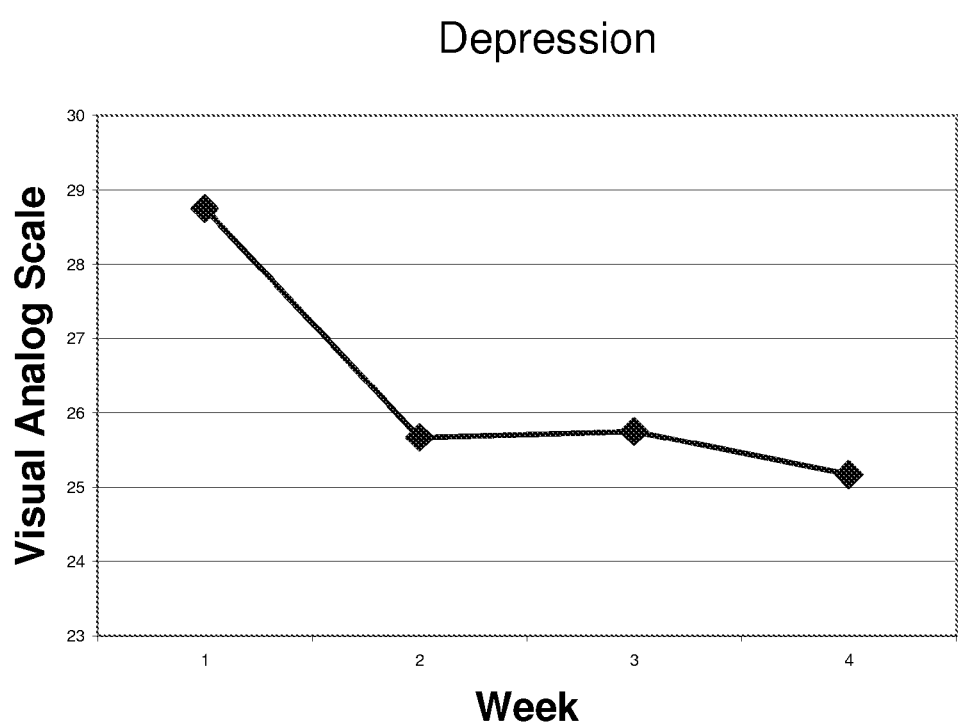
FIG. 2 is a chart showing changes in subjects' experience of depression during the study described in Example 1.
Figure 3:
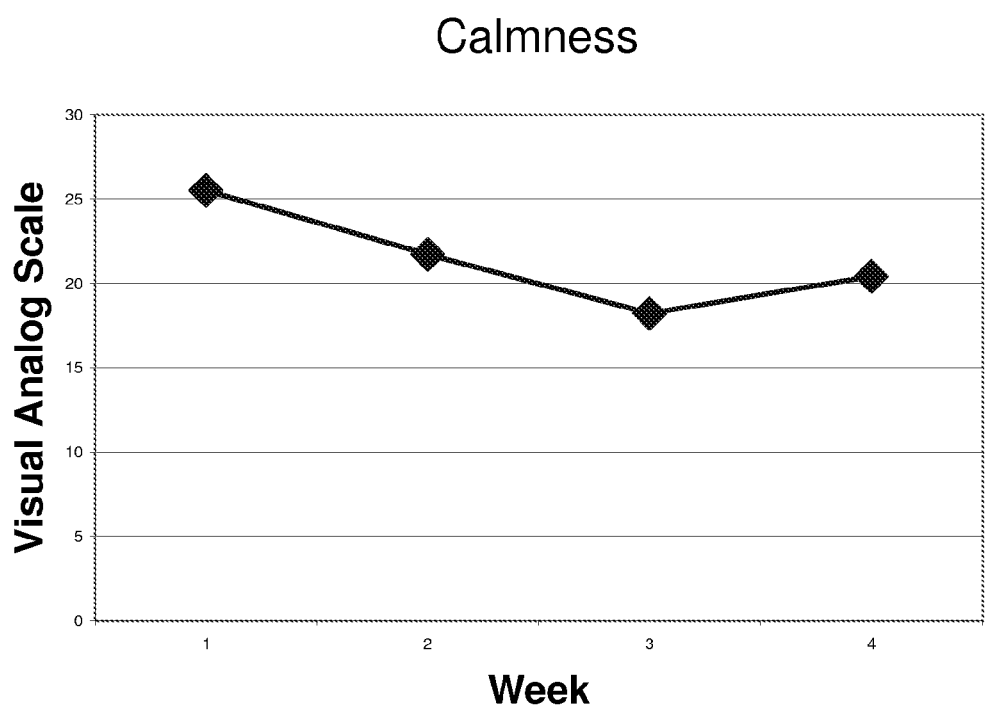
FIG. 3 is a chart showing changes in subjects' experience of calmness during the study described in Example 1.
Figure 4:
FIG. 4 is a chart showing changes in subjects' experience of hunger during the study described in Example 1.

All dimensions specified in this disclosure are by way of example only and are not intended to be limiting. Further, the proportions shown in these Figures are not necessarily to scale.

DESCRIPTION

Definitions

"About" means within 15% of a recited number.

"BMI" or body mass index is defined as weight of an individual in kilograms divided by the square of the individual's height in meters.

"Diet" means the foods consumed by an individual over a particular period of time, such as over the course of a day or week, or at a meal.

"Food" refers to a solid, liquid, gel, or other substance which provides nourishment, in particular to a human subject.

"Fat" refers to both fats and fatty acids, unless otherwise specified.

"Meal" refers to the food consumed over a limited period of time. A meal can comprise, for example, solely the present food composition or the present composition in combination with other food.

"Overweight" refers to an individual having a body mass index (BMI) of between 25 and 30, and "obese" refers to an individual having a BMI of 30 or greater.

"Oral" administration generally refers to consumption of food and/or beverages via the mouth, but also includes other methods of nutrient delivery into the gastrointestinal tract, such as enteral administration.

"Processed food" refers to food which has been preserved so that it does not spoil and/or lose another desired property (such as color or flavor) as quickly as unprocessed food.

"VAS" or "Visual Analogue Scale" is a measurement instrument for measuring a characteristic, such as hunger or pain, that ranges across a continuum of values. Values corresponding to the magnitude of the characteristic as experienced by a subject are recorded by the subject at particular points in time in studies which make use of a VAS.

"Weight control" refers to a predetermined action or set of actions which results in weight maintenance, weight loss, or weight gain less than would be anticipated.

As used herein, the term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Food Compositions

The present compositions and methods are believed to counter the effects of calorie restriction on the metabolic rates of individuals who are trying to lose weight by leveraging the thermogenic effect that n–3 polyunsaturated fatty acids, in particular docosahexaenoic acid (DHA), have when added to meal replacement diets having appropriate amounts of proteins and other nutrients. The present compositions and methods are also believed to increase satiety and compliance by stimulating homeostatic mechanisms in the ileum. Increased satiety can enhance a subject's adherence to a diet, thereby accelerating weight loss and improving weight maintenance.

Prior art meal replacements have not been specifically formulated with sufficient amounts of omega-3 fatty acids and protein to appropriately accelerate weight loss in overweight and obese individuals. In the present compositions, an appropriately high amount of protein is included together with one or more omega-3 fatty acids. While omega-3 fatty acids such as α-linolenic acid (ALA) and eicosapentaenoic acid (EPA) can be used in the present compositions, DHA is preferably chosen as the omega-3 fatty acid component.

Other fat sources used in the present formulations can be in the form of fats and/or fatty acids, and can comprise monounsaturated fat and/or saturated fats. While trans fats can be used, they are not preferred, as they have been associated with an increased risk for heart disease. Fats and fatty acids used in the present composition can be derived from any nutritionally acceptable source, and can be derived from animal, vegetable, or other sources.

The protein and carbohydrate components of the present composition can be derived from any nutritionally acceptable source, and can likewise be derived from animal, vegetable, or other sources. Examples of acceptable protein ingredients include soy protein and whey protein. A carbohydrate component in the formulation, while not absolutely required, improves mental functioning, helps prevent profound diuresis and subsequent low blood pressure, helps maintain muscular strength, and helps prevent against loss of lean body mass.

In addition, vitamins and minerals are preferably included in the present compositions in order to provide a balanced, nutritious meal replacement product. Essential vitamins are preferably included, including one or more of the following: Vitamin A, Vitamin C, Vitamin B1, Vitamin B2, niacinamide, Vitamin D, Vitamin E, Vitamin B6, folic acid, Vitamin B12, biotin, pantothenic acid, and Vitamin K. The present composition also preferably includes one or more of the following minerals: phosphorus, iodine, magnesium, zinc, copper, manganese, chromium, molybdenum, calcium, potassium, sodium, and iron. Other food components, such as fiber and cholesterol, can also be included in the present composition.

Such additives can be used at any safe level, but preferably are present at between about 16% and 33% of the minimum recommended daily intake (RDI) levels established by the Food and Nutrition Board of the National Academy of Sciences and/or by the U.S. Federal Food and Drug Administration, and more preferably at between about 20% and 25%. Compositions having such vitamin and mineral levels, for example, are more appropriately used as complete meal replacements in a weight control program.

The ratio between the number of protein calories and the combined number of carbohydrate and fat calories in the present food composition is at least 0.5:1. Higher ratios of protein calories to carbohydrate and fat calories are preferred, such as about 0.6:1, about 0.7:1, about 0.8:1, about 0.9:1, about 1:1, about 1.2:1, and about 1.5:1, for example. An especially preferred embodiment of the present food composition has a ratio of about 1.6:1, and higher ratios are also possible. In order for the present food composition to be used as a meal replacement product, sufficient carbohydrate and fat components are preferably present in the composition in order to provide for the nutritional needs of an individual consuming this food composition. If the present composition is used as a supplement to an individual's diet rather than as a meal replacement, the foregoing ratios of protein calories to carbohydrate and fat calories are preferably maintained with respect to a meal at which the present food composition is consumed and/or with respect to the overall diet of the individual over the course of a particular time period, such as a day, week, or month.

In one embodiment, a serving of the present food composition can have between about 60 and 300 calories and the following nutritional components: between 6 and 35 grams of protein; between 0 and 30 grams of carbohydrate; and between 0 and 6 grams of fat. In another embodiment, a serving of the present food composition can comprise about 15 grams of protein; about 7-8 grams of carbohydrate; and about 1-2 grams of fat. In a another embodiment, the present food composition has, in a serving, about 15 grams of protein; about 15 grams of carbohydrate; and between 1 and 6 grams of fat. A particularly preferred embodiment of the present food composition comprises a serving of about 100 calories having 15 grams of protein, 7 grams of carbohydrate, and 1 gram of fat.

In the foregoing embodiments, the fat component preferably comprises between about 100 and about 1000 milligrams of an omega-3 fatty acid such as DHA. DHA in such embodiments is preferably present in amounts of between about 200 and 400 mg, more preferably between about 210 and 270 milligrams, and is preferably about 250 milligrams.

The foregoing embodiments of the present food composition are formulated to serve as a single serving meal replacement and/or meal supplement for administration five times a day to an individual seeking or in need of weight loss or weight control, and can serve to completely or partially replace other food in an individual's diet for a limited period of time. In order for a food composition to be used for weight control or weight loss, it is preferably used as a total replacement for one or more meals each day over a period of time, and preferably for all meals over a predetermined period of time. The present composition is therefore preferably formulated with flavorings and other ingredients known to the art in order to make it palatable. Preferably, such ingredients do not provide a significant source of calories, and more preferably do not provide any additional calories.

Weight Control Methods

The present methods are believed to lead to a greater decrease in body mass index (BMI) than current dietary regimens. Subjects who can benefit from the present compositions and methods include, in particular, those determined to be obese or overweight. In the present weight control methods, one or more omega-3 fatty acids such as DHA are administered orally to a subject as part of a high-protein diet, at doses of between about 100 and about 1000 mg per serving. Preferably, an amount of DHA of between 300 milligrams and 2500 milligrams is consumed by a subject daily, more preferably an amount of between about 1000 and 1800 milligrams is consumed, and even more preferably about 1100 milligrams is consumed. Preferably, such omega-3 fatty acids are consumed a plurality of times over the course of a day by a subject, and most preferably at every meal.

In order to facilitate weight loss, a subject treated according to the present methods preferably consumes the present food composition as described above, either solely or in combination with other food. The ratio between the number of protein calories and the combined number of carbohydrate and fat calories in the present food composition and/or in the subject's diet during treatment is at least 0.5:1. Higher ratios of protein calories to carbohydrate and fat calories are preferred, such as about 0.6:1, about 0.7:1, about 0.8:1, about 0.9:1, about 1:1, about 1.2:1, and about 1.5:1, for example. A ratio of about 1.6:1 is especially preferred, and higher ratios are also possible.

The total number of calories consumed by a subject in a day in connection with practicing the present methods is preferably between 800 and 1200, i.e. a Low Calorie Diet (LCD), and more preferably is 800 or less, i.e. a Very Low Calorie Diet (VLCD). A subject practicing the present methods preferably consumes 4 to 6 servings of the present meal replacement composition per day in order to manage appetite, although the composition can also be consumed in a different number of servings, such as three servings, as long as the total number of calories does not exceed a predetermined amount for the subject (for example, to maintain a LCD or VLCD).

The present composition can be administered to a subject in any of a variety of forms, such as in a liquid solution or suspension, or as a solid, e.g. in the form of a snack bar. In one preferred form, the composition is provided in powder form, and can be reconstituted in water. In this form the composition can be provided in bulk or in packages corresponding to an individual serving, such as in an amount of about 100 calories.

The meal replacement composition preferably comprises a complete and nutritionally balanced food product so that subjects can limit their food intake to only the present meal replacement composition for a period of time, preferably at least a week, more preferably at least two weeks, and even more preferably at least a month. Such subjects are preferably monitored by a physician or other health professional while consuming the present food compositions in order to ensure that they do not develop any electrolyte abnormalities from the ensuing diuresis resulting from the weight loss and to adjust downward medications used to control hypertension, diabetes, or hypercholesterolemia.

EXAMPLES

Example 1

Weight Control Program

Twelve (12) subjects were recruited to evaluate the present method. The average age was 49 and ranged from 33 to 64. There were 4 females and 8 males. The mean BMI was 38.5 and the range was 32.28 to 53.17. Ten subjects completed all assessments.

Prior to starting on the trial, baseline height and weights were obtained and body mass index calculated using the formula weight (in kg.)/height (in meters) squared. All 12 subjects were either overweight or obese at baseline with body weights ranging from 192 to 379, with the average being 261, and BMI scores ranging from 29.90 to 53.17, with the average being 38.53.

Subjects were provided two meal replacement food compositions in liquid form having different formulations. The formulations were equivalent with respect to calories and with respect to the ratio of protein calories to (carbohydrate+fat) calories (ratio=1.7:1). Both formulations included the following ingredients: calcium caseinate, maltodextrin, fructose, soy oil, potassium citrate, natural and artificial flavors, salt, vitamin and mineral premix (contained 1% or less of Vitamin A Palmitate, ascorbic acid, d,L-alpha tocopheryl acetate, reduced iron, niacinamide, zinc oxide, d-calcium panthothenate, pyridoxine hydrochloride, copper gluconate, riboflavin, thiamin, mononitratem folic acid, botin, potassium iodide, cyanocobalamin) cellulose gum, SUCRALOSE®, and acesulfame potassium. This formulation is available as PRO-MED from Nutritional Resources, Augusta, Ga.

The nutritional components of these formulations are set out in Table 1 below.

TABLE 1

Serving Size: 1 Bottle (26 g)
Amount per serving: Calories 100
Calories from Fat 10

| FOOD COMPONENT | TOTAL GRAMS | % DAILY VALUE |
|---|---|---|
| Total Fat | 1 g | 1% |
| Saturated Fat | 0 g | |
| Trans Fat | 0 g | |
| Cholesterol | <5 mg | 1% |
| Sodium | 170 mg | 7% |
| Potassium | 250 mg | 7% |
| Total Carbohydrate | 7 g | 2% |
| Dietary Fiber | 0 g | 0% |
| Sugars | 3 g | |
| Protein | 15 g | |
| Vitamin A | | 50% |
| Vitamin C | | 40% |
| Calcium | | 25% |
| Iron | | 35% |

The study formulation comprised, in addition, 233 mg DHA derived from a non-fish marine source (Martek, Columbia, Md.) in each serving. For Week 1, subjects were instructed to consume 5 vanilla-flavored shakes as described above, each containing 100 calories and no DHA. They were also instructed to eat two frozen, prepared meals from an approved list per day and one snack, an OPTIFAST nutrition bar (available from Novartis, Basel, Switzerland), both as described in Table 2 below. In weeks 2, 3, and 4, standard shakes were replaced with shakes enriched with DHA and subjects continued to consume one prepared meal and one snack per day.

TABLE 2

| | TOTAL CALORIES | PROTEIN (g) | CARBOHYDRATE (g) | FAT (g) |
|---|---|---|---|---|
| "Average" Meal (average of medians) with two meals taken per day | 255 | 17.5 | 32.25 | 6.25 |
| Optifast Bar | 160 | 14 | 23 | 4 |

The subjects consumed approximately 1165 mg DHA and 1120-1220 calories per day. The average meal (taken as an average of medians of each category of entrée, i.e., fish, chicken, beef, and pasta) had a ratio of protein/carbohydrate+fat of 0.726:1, with meals ranging from 230 to 280 calories (the mean being 255 calories).

Subjects were provided a log in which they recorded subjective hunger, satiation, calmness, depression, and energy using 100 millimeter visual analog scales (VAS) five times per day. Assessments were performed as follows: prior to breakfast; prior to lunch; mid-afternoon; prior to dinner; and prior to bed. Body weight measurements were performed on the same scale weekly at the time of their office visits.

An analysis of variance with repeated measures (over time) was obtained for each of the variables studied using the average score for the week. Differences were significant at a $p<0.05$. Post hoc t-tests were performed on the significant variables. Calculations were performed using OPENSTAT4 program and Microsoft Excel Statistics Module. Table 3 summarizes the results for each of the measures by subject by week with the corresponding F score and P value.

TABLE 3

| Variable | Week 1 | Week 2 | Week 3 | Week 4 | F | P |
|---|---|---|---|---|---|---|
| Fullness | 35.83 | 41.67 | 44.08 | 47.25 | 7.73 | <.0001 |
| Depression | 28.75 | 25.67 | 25.75 | 25.17 | 0.54 | 0.79, NS |
| Calm | 25.5 | 21.7 | 18.2 | 20.4 | 2.27 | 0.10, NS |
| Hunger | 52.42 | 52.58 | 48.83 | 45.83 | 1.86 | 0.16, NS |
| Fatigue | 45.55 | 47 | 47.36 | 47.36 | 0.34 | 0.35, NS |

A significant effect by time was observed in Fullness ($F=7.73$, $p<0.001$). Post hoc pairwise comparisons revealed significant differences in Fullness between Week 1 and Week 3, and between Week 1 and Week 4. Subjects reported feeling significantly more full on the DHA augmented meal replacement than on the standard product.

A significant effect in weight over time ($F=10.51$, $p<0.001$) was also recorded. Post-hoc comparisons between the mean weights by week revealed significant decreases in weight when the baseline was compared with Week 1, Week 2, Week 3, and Week 4. No other pairwise differences between the weeks were noted.

Example 2

Alternative Weight Control Program

A subject practices a dietary regimen as follows in order to control the subject's weight. The subject consumes one serving of a composition having the following characteristics, 5 times per day, at regular intervals during waking hours, for four weeks:
 About 102 total calories;
 15 grams of protein;
 7 grams of carbohydrate;
 1 gram of fat of which 230 mg is EPA; and
 vitamins and minerals in amounts corresponding to 20% of the daily RDI for such vitamins and minerals.

Although the present invention has been discussed in considerable detail with reference to certain preferred embodiments, other embodiments are possible. The steps disclosed for the present methods are not intended to be limiting nor are they intended to indicate that each step depicted is essential to the method, but instead are exemplary steps only. Therefore, the scope of the appended claims should not be limited to the description of preferred embodiments contained in this disclosure. All references cited herein are incorporated by reference to their entirety.

What is claimed is:

1. A method of inducing weight loss by increasing satiety of a subject, comprising orally administering docosahexaenoic acid (DHA) to the subject in an amount of at least 1100 milligrams per day in a diet comprising between about 800 calories and about 1200 calories per day which comprises protein, carbohydrate, and fat, wherein the number of calories provided by protein in the diet compared to the number of calories provided by carbohydrate and fat produces a ratio of at least 0.5:1, thereby resulting in increased satiety.

2. The method of claim 1, wherein up to about 1800 milligrams of DHA per day is administered to the subject.

3. The method of claim 1, wherein up to about 2500 milligrams of DHA per day is administered to the subject.

4. The method of claim 1, wherein the DHA is administered to the subject in a plurality of servings, and wherein each serving comprises at least about 230 milligrams of DHA.

5. The method of claim 1, wherein the DHA is administered to the subject in a plurality of servings, and wherein each serving comprises at least about 400 milligrams of DHA.

6. The method of claim 1, wherein the step of orally administering DHA comprises administering a food composition five times per day, the food composition comprising about 100 calories and about 230 milligrams of DHA.

7. The method of claim 1, wherein the ratio of the number of calories provided by protein in the diet compared to the number of calories provided by carbohydrate and fat in the diet is between about 0.7:1 and about 1.6:1.

8. The method of claim 1, wherein the DHA is present in a nutritional composition in powder form which is reconstitutable in water.

9. The method of claim 1, wherein the DHA is present in a nutritional composition comprising a liquid solution or a suspension.

10. The method of claim 1, wherein the DHA is administered to the subject for at least 2 weeks.

11. The method of claim 1, wherein the DHA is administered to the subject for at least 4 weeks.

12. The method of claim 1, wherein the DHA is present in a nutritional composition in the form of a snack bar.

* * * * *